(12) United States Patent
Macnamara (10) Patent No.: US 8,567,033 B2
(45) Date of Patent: *Oct. 29, 2013

(54) METHOD OF CONSTRUCTING AN ARTICULATION JOINT FOR STEERABLE MEDICAL DEVICE

(75) Inventor: Francis T. Macnamara, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 26 days.

This patent is subject to a terminal disclaimer.

(21) Appl. No.: 13/227,878

(22) Filed: Sep. 8, 2011

(65) Prior Publication Data

US 2012/0137491 A1 Jun. 7, 2012

Related U.S. Application Data (63) Continuation of application No. 11/735,875, filed on Apr. 16, 2007, now Pat. No. 8,037,590.

(60) Provisional application No. 60/795,119, filed on Apr. 14, 2006.

(51) Int. Cl.
*A61B 1/008* (2006.01)
*B21D 39/00* (2006.01)

(52) U.S. Cl.
USPC ............. 29/505; 29/525.14; 29/557; 600/141

(58) Field of Classification Search
USPC ............... 29/505, 525.14, 557; 600/149, 141; 72/368, 369, 370.14, 370.27
See application file for complete search history.

(56) References Cited

U.S. PATENT DOCUMENTS

| | | | |
|---|---|---|---|
| 4,796,607 A | 1/1989 | Allred, III et al. | |
| 4,834,069 A | 5/1989 | Umeda | |
| 5,005,558 A | 4/1991 | Aomori | |
| 5,157,826 A * | 10/1992 | Porter et al. | 29/439 |
| 8,037,590 B2 * | 10/2011 | Macnamara | 29/460 |

FOREIGN PATENT DOCUMENTS

DE 3408432 A * 9/1985

* cited by examiner

*Primary Examiner* — Jermie Cozart
(74) *Attorney, Agent, or Firm* — Bookoff McAndrews, PLLC

(57) ABSTRACT

A method of constructing an articulation joint includes forming a metallic tube with a number of rings formed therein. Springs may be secured to the inside surface or outside surface of the rings to allow the joint to bend in directions transverse to the axis of the springs. A fixture may be used to hold the springs at the correct position within the tube and the springs may be urged toward the rings or vice versa to obtain a good bond between the springs and the rings.

17 Claims, 11 Drawing Sheets

METHOD OF CONSTRUCTING AN ARTICULATION JOINT FOR STEERABLE MEDICAL DEVICE

CROSS-REFERENCE(S) TO RELATED APPLICATION

This application is a continuation of U.S. application Ser. No. 11/735,875, filed Apr. 16, 2007, now U.S. 8,037,590 B2 and claims the benefit of U.S. Provisional Application No. 60/792,119, filed Apr. 14, 2006, the disclosure of all of which are hereby incorporated by reference.

FIELD OF THE INVENTION

The present invention relates generally to medical devices, and particularly to steerable, minimally invasive devices.

BACKGROUND

As an alternative to performing more invasive surgical procedures, many physicians are using minimally invasive devices to view, diagnose, and treat internal body tissues of patients. Such minimally invasive devices include catheters, endoscopes and like devices having a flexible shaft that may be directed to a region of interest within the patient's body. The shaft generally includes one or more lumens through which tools, liquids/medications and air/vacuum can be passed. In addition, many such devices include steering to allow the device to be selectively oriented in the body and imaging capabilities to view a tissue site.

In order to reduce the risks associated with the use of a medical device in the body, many such devices are becoming disposable. For each use, a physician can obtain a new, sterilized device prior to the examination and/or treatment of a patient. Upon completion of a procedure, the device can be disposed of, thereby eliminating any chance of cross-contamination between patients.

One factor in limiting the ability to make steerable catheters and endoscopes disposable is the cost of an articulation joint in the device. The articulation joint aids in bending the distal tip under tension of one or more control wires within the device. In addition, the articulation joint maintains the stiffness of the shaft in a longitudinal direction and transmits rotational torque applied by the physician. Traditionally, articulation joints are made of a number of riveted stainless steel components that are expensive and laborious to manufacture.

Therefore, there is a need for a method of creating an articulation joint for use in steerable, minimally invasive devices that allow the devices to be manufactured inexpensively enough so that they can be considered disposable.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Embodiments of the present invention are directed to articulation joints and methods of creating articulation joints for use in a steerable medical device such as an endoscope or a catheter. In one aspect of the present invention, an articulation joint includes a tubular structure having a number of axially aligned rings formed therein. In one embodiment, the rings are formed from a metallic tube, while in another embodiment, the rings are formed from a flat, metal sheet which is rolled into a tubular structure. A fixture that supports a number of springs is inserted into the tube. The springs are positioned close to the inside surface of the rings such that they can be bonded to the rings. Upon bonding the springs to the rings, the fixture is removed from the articulation joint.

In accordance with another aspect of the present invention, a mechanism for use in assembling an articulation joint is provided. The mechanism comprises a fixture for supporting a number of springs within a metallic tube having a number of rings, means for urging the springs and the walls of the rings together, and an energy source for bonding the rings to the springs supported by the fixture.

In accordance with another aspect, a method of constructing an articulation joint for a steerable medical device is provided. The method comprises the steps of: forming a tubular structure including a number of axially aligned rings, wherein each axially aligned ring defining a plurality of slots spaced equidistant around the circumference of the ring; placing a plurality of springs into aligned slots of adjacent axially aligned rings; and securing the springs to the adjacent axially aligned rings.

In accordance with another aspect of the present invention, a method of constructing an articulation joint for a steerable medical device is provided. The method comprises the steps of: obtaining a sheet of metal stock; forming a pattern of ring segments into the sheet of metal stock; forming a tubular structure from the sheet of metal stock; and attaching a number of springs to the ring segments.

DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION

Embodiments of the present invention will now be described in detail with reference to FIGS. 1-13B where like numerals correspond to like elements. As indicated above, embodiments of the present invention are directed to articulation joints and methods of manufacturing articulation joints for steerable medical devices, such as catheters, endoscopes, or the like. Embodiments of the present invention may be useful for manufacturing an articulation joint of the type shown in FIGS. 1A and 1B (which is also disclosed in U.S. patent application Ser. No. 10/811,781, filed Mar. 29, 2004 and herein incorporated by reference).

In this embodiment, an articulation joint 10 is a tubular structure comprised of a number of rings 12b, 12c, 12d . . . , etc., interconnected between proximal and distal rings 12a and 12o, respectively. The rings 12a, 12b, 12c, . . . 12o, etc., are joined together by pairs of springs 14a, 14b, 14c, etc. In the example shown in FIG. 1A, the joint 10 starts out as a solid tube and a high speed laser is used to cut a precise pattern to create individuals rings. Each pair of adjacent rings (12a-12b, 12c-12d, 12e-12f, etc.) are held together with a pair of springs (e.g., 14a, 14c, 14e, etc.) that are positioned 180° apart on the rings. Similarly, adjacent pairs of rings (e.g., 12b-12c, 12d-12e, 12f-12g, etc.) are held together with a pair of springs (14b, 14d, 14f, etc.), which are oriented at 90° with respect to the springs 14a, 14c, 14e, etc., in the manner shown in FIG. 1A. This alternating pattern of springs allows each pair of rings to bend in one of two directions that are oriented at 90° apart with respect to the longitudinal axis of the articulation joint 10.

In the embodiment shown, each ring in the body of the articulation joint 10 (that is between the distal 12a and the proximal ring 12o) has a top and bottom rim which is not planar with respect to the longitudinal axis of the ring, but varies around the ring. As best shown in FIG. 1B, each ring (only ring 12b is shown in FIG. 1B) is formed with a top rim 20 that peaks at a pair of high edges 22 positioned approximately 180° apart on the ring. The rim slopes away from the high edges 22 to a pair of low edges 24 that are oriented at approximately 90° to the high edges 22. Similarly, the bottom rim 26 of the ring has a pair of high edges 28 oriented in the same directions as the low edges 24 on the top rim 20. The bottom rim 26 slopes away from the high points 28 to a pair of symmetric low edges 30 that are oriented with the high edges 22 on the top rim 20.

In the embodiment shown, the rims slope at an angle of 14° from the high edges 22 and 26. The rim angle may be consistent for all rings in the articulation joint or alternatively it is possible to vary the rim angle from one end to the other. For example, the angles may be varied so that the joint bends more toward one end (e.g., toward the ring 12a or toward ring 12o) of the articulation joint such that the joint has a radius of curvature that varies along the length of the joint. The result can also be such that the rings of the joint toward the distal ring 12a bends before the rings of the joint toward the proximal ring 12o when tension is applied to the control wires. In another embodiment, the rim angles may be varied so that the articulation joint can bend further in one direction than in another. For example, the rim angles could be chosen so that the joint bends further in the left, right directions than in the up, down directions, or vice versa.

Figure 1A:
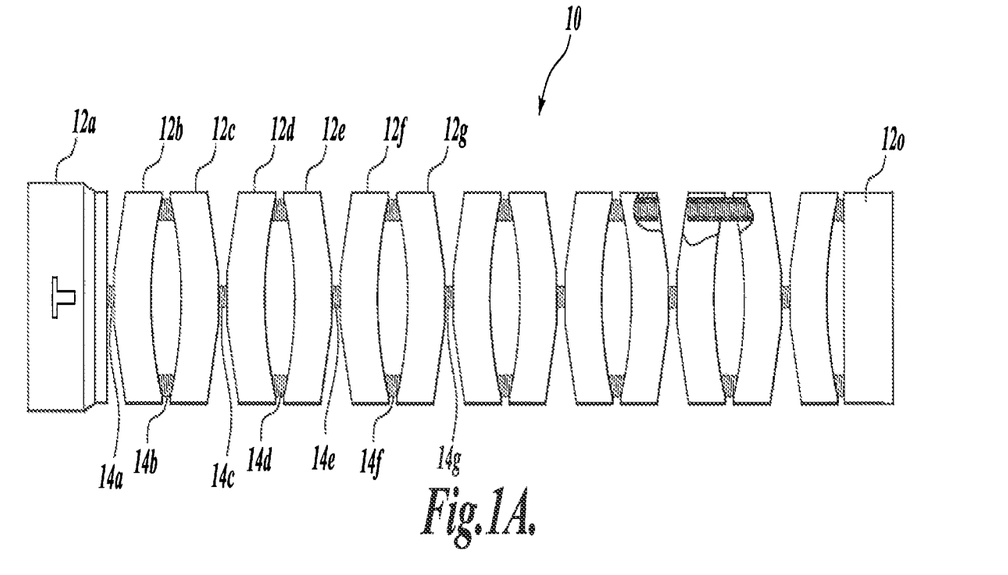
FIGS. 1A and 1B illustrate one embodiment of an articulation joint that can be manufactured according to aspects of the present invention.
Figure 1B:
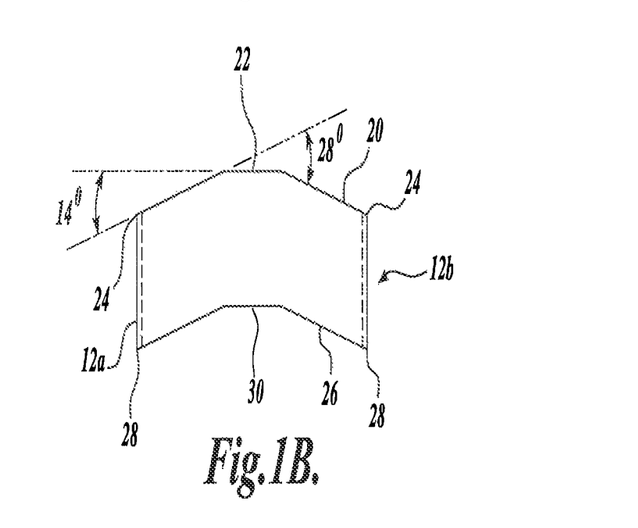

As shown in FIG. 1A, when properly aligned such that the sloped rims of adjacent rings angle away from each other, an increased bending between the adjacent rings can be achieved. In contrast, traditional articulation joints have straight rims so the increased bending can only be derived by either increasing the gap between the links or including more links. Increasing this gap makes the articulation joint less stable, which results in decreased column strength and support to the inner tubes during articulation while including more links increases the cost.

Figure 2:
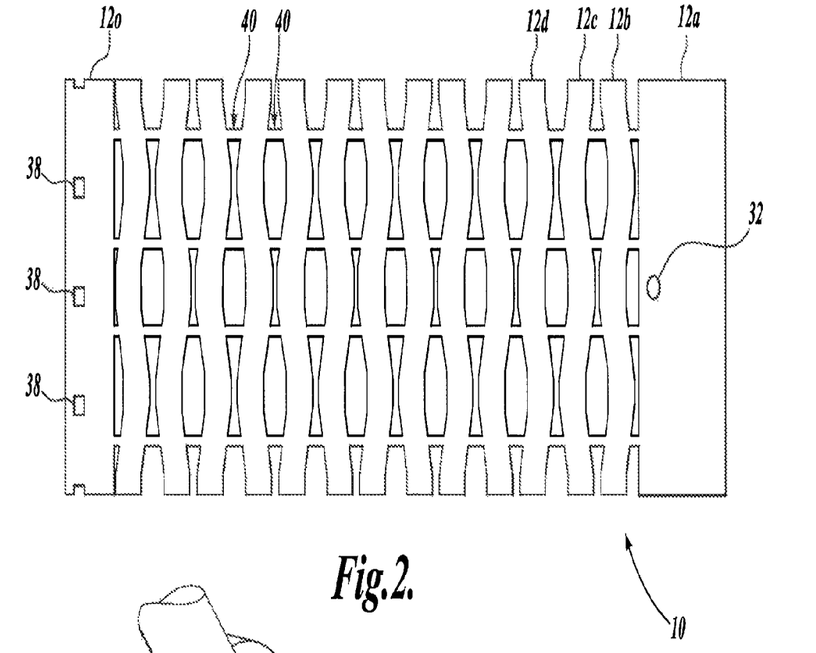
FIG. 2 illustrates further detail of the pattern of rings in the articulation joint shown in FIG. 1A.

FIG. 2 illustrates the ring pattern cut into the tubular structure if the tubular structure is cut along its length and flattened. The articulation joint includes a distal most ring 12a and a proximal ring 12o wherein each of the sloped rings 12b, 12c, 12d, etc., are between the distal and proximal ring.

The distal ring 12a may include one or more holes 32 positioned around the distal ring 24 to allow components to be secured to the distal ring. In addition, the distal ring 12a may include one or more lances (not shown) that serve as stops for the distal ends of a control wire. The proximal ring 12o may include one or more holes 38 that are used for securing components to the proximal ring 12o.

To keep the articulation joint together as it is being assembled, the cutting is done in two stages. One or more struts or tabs 40 remain to hold the rings together until the springs are bonded to the rings. Once the springs are bonded to the rings, the tabs 40 may be removed from between the rings to allow the articulation joint to bend freely. As will be described below, the tabs 40 may be removed via any appropriate technique, such as laser cutting, water jet cutting, wire EDM, stamping, etc.

Figure 3:
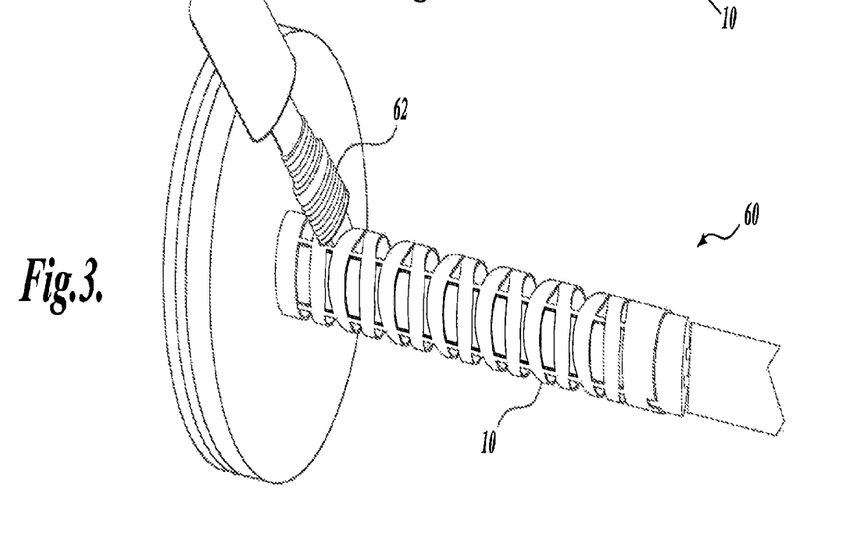
FIG. 3 illustrates springs being bonded into an articulation joint with a rotatable fixture in accordance with an embodiment of the present invention.

To complete the articulation joint 10, the springs 14 are bonded to the inside of the rings 12 in order to allow the rings 12 to bend with respect to each other. In one embodiment, the springs 14 are placed on a mechanism such as is shown in FIG. 3, which rotates the springs 14 and rings 12 under a laser 62 that welds the springs 14 to the rings 12 of the articulation joint 10. In addition, the laser removes the tabs 40 that join the individual rings together. Alternatively, these tabs can be removed via a secondary process such as punching, wire EDM, stamping, etc.

Figures 4, 5:
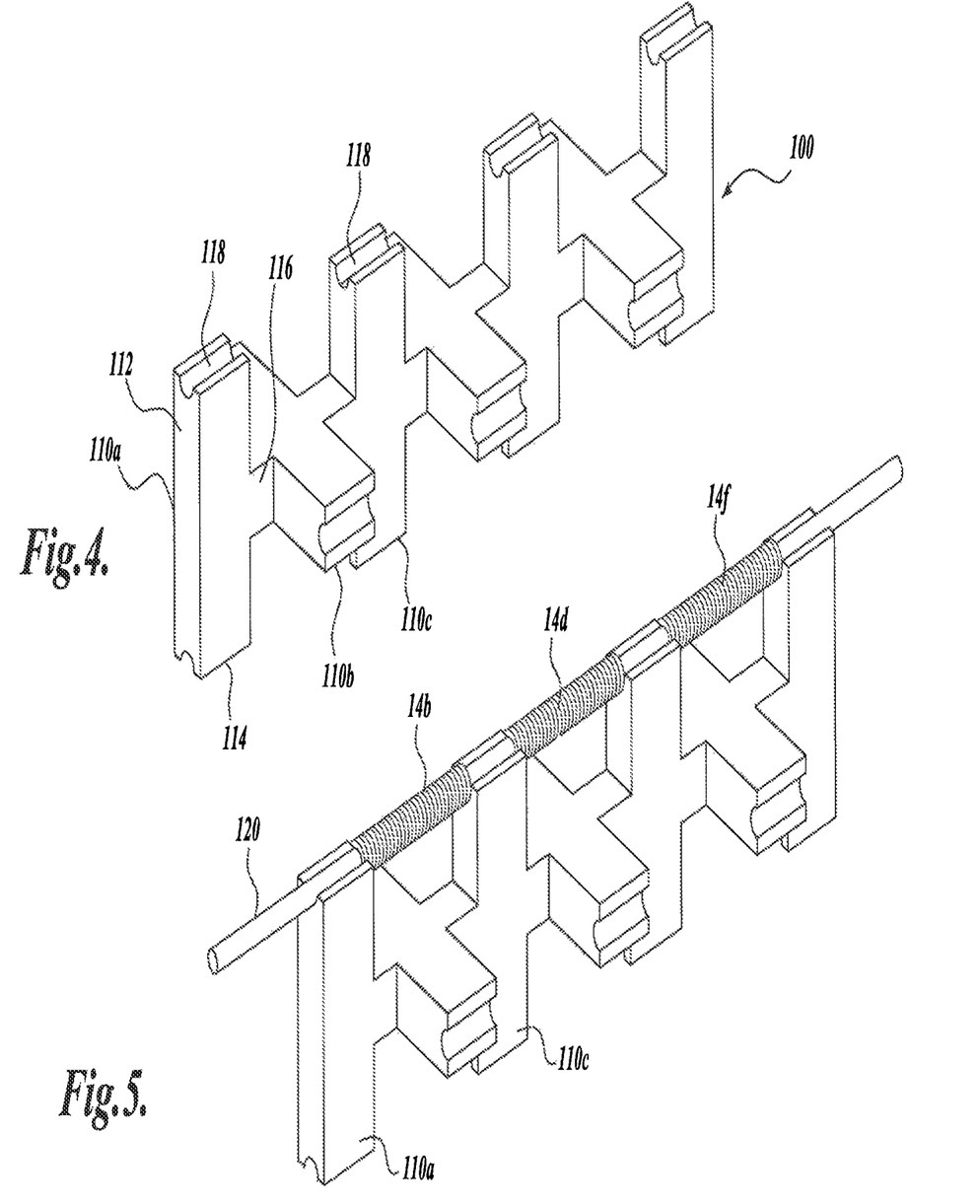
FIG. 4 illustrates one embodiment of a fixture for supporting a number of springs within an articulation joint in accordance with the present invention.
FIG. 5 illustrates a number of springs supported by the fixture shown in FIG. 4.

FIG. 4 illustrates one embodiment of a fixture 100 that supports a number of springs within the articulation joint 10 during manufacture. The fixture 100 includes a number of spring supports 110a, 110b, 110c, etc., that are alternately oriented at 90 degrees with respect to each other along the length of the fixture. Each spring support 110 has a generally T-shaped configuration with arms 112, 114, that extend radially outward from the longitudinal axis of the fixture, and a center leg 116 oriented along the longitudinal axis of the fixture that connects the support to an adjacent support. The arms 112, 114 also include a groove 118 oriented lengthwise along the fixture into which a wire mandrel is placed during manufacture of the articulation joint.

As shown in FIG. 5, a wire mandrel 120 extends through the center of a number of helical springs 114b, 114d, 114f, etc. Each of the springs rest in the area between the arms of alternate spring supports that are oriented in the same direction. For example, spring 114b is positioned by the wire mandrel 120 in a space between the radially extending arms of spring supports 110a and 110c. While not shown, it will be appreciated that additional wire mandrels and springs are positioned in the other grooves of the support arms such that each ring in the articulation joint is secured to two springs and that the pairs of springs in the articulation joint are alternately angled at 90° with respect to each other along the length of the fixture.

In one embodiment, the arms 112, 114 of the spring supports 110 are sized to allow the springs and wire mandrels to be easily inserted into the tubular structure of the articulation joint. Once the fixture 100 is loaded with the springs that are supported by the individual wire mandrels 120 and inserted into the tubular structure that forms the rings of the articulation joint, the entire assembly is secured to a rotating mechanism such as an electric motor with a chuck as shown in FIG. 3. A laser 62 may be used to bond the springs to the individual rings by spot welding or the like. The articulation joint may move beneath the laser in order to weld all the springs. Alternatively, the laser may be moved with respect to the articulation joint.

In one embodiment, prior to bonding the springs to the rings, the springs may be urged towards the interior surface of the rings that form the articulation joint. For example, a roller (not shown for ease of illustration) that applies external pressure is placed on a ring to press the individual rings against the springs on the mandrel. The laser 62 or other energy source may then be used to bond, e.g., spot weld, the springs to the inner surface of the rings while the roller ensures contact between the two components. In addition, the laser may be used to remove the tabs 40 joining adjacent rings, such that the articulation joint may be able to bend.

Other mechanisms for causing the springs to be positioned close enough to the rings to allow them to be bonded securely include mechanically, pneumatically, or hydraulically movable arms on the fixture that force the spring segments radially outward. Heat activated arms may be used to expand the arms and bring the springs closer to the inner surface of the rings. Conversely, the rings may be cooled by the application of a cold gas or liquid to constrict the rings onto the springs.

Once the springs are bonded to the rings, the wire mandrels 120 are removed and the fixture 100 is withdrawn from the articulation joint 10.

Figure 6:
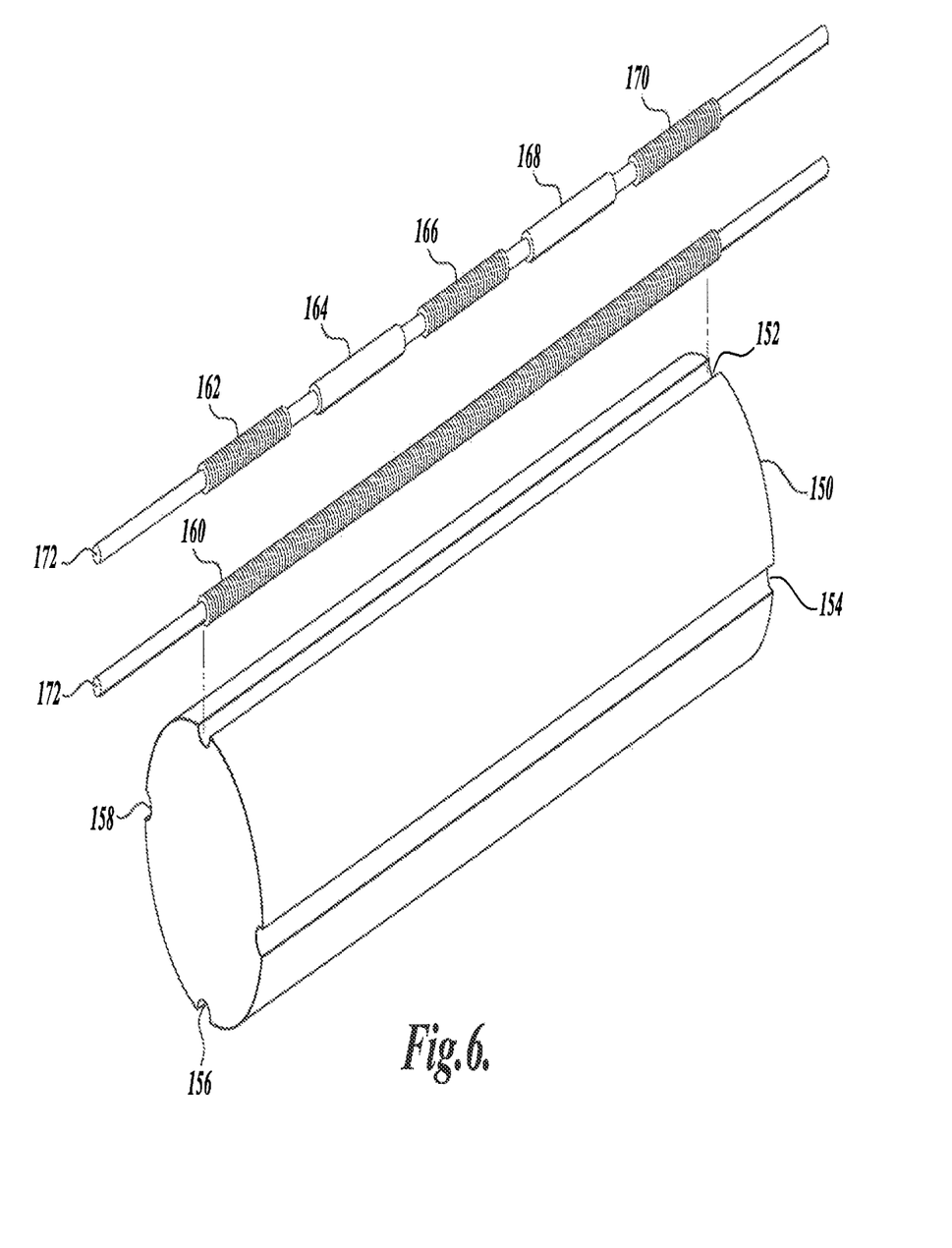
FIG. 6 shows an alternative embodiment of a fixture for use in supporting springs within an articulation joint in accordance with the present invention.

FIG. 6 shows an alternative embodiment of a fixture 150 that can be used to hold the springs in position for bonding to the interior surface of the rings of the articulation joint 10. In this embodiment, the fixture 150 comprises a generally cylindrical member having a number of longitudinally extending channels 152, 154, 156, 158 positioned around the circumference thereof. The channels 152-158 are sized to receive a spring therein. In the embodiment shown, a spring 160 can be a continuous length of spring. Alternatively, the spring can comprise a number of spring segments 162, 166, 170, that are separated by spacers 164, 168. Each of the springs (and spacers if present) may be held in place by a wire mandrel 172. Alternatively, to reduce manufacturing time required to thread each spring over the mandrel, the channels can hold the springs in their proper position for bonding, e.g., welding, without requiring a mandrel, Upon insertion of the fixture 150 into axial aligned rings of the articulation joint tubular structure, the springs may be urged against the inner surface of the rings or vice versa, and the springs are bonded to the rings with a laser or other suitable bonding means. If a continuous spring 160 is used, the spring can be cut with a laser, electro discharge machining or the like, in the area between the rings in order to remove those portions of the spring that may inhibit bending of the articulation joints. Alternatively, a variable pitch spring may be used where an allowance is made on the increased pitch section for the spring to compress and allow the links to bend relative to each other without having to remove any material. If the individual spring segments 162, 166, 170 are used, the articulation joint can bend by removal of the wire mandrel 172 (if used) and the fixture 150 from the tube of the articulation joint.

An advantage of using the spring segments 114*b*, 114*d*, 114*f*, etc., shown in FIG. 5 or the spring segments 162, 166, 170, shown in FIG. 6 is that the spring bending coefficients can be tailored such that the articulation joint has different bending characteristics at any point along its length. For example, the articulation joint may become more flexible toward the distal tip. The flexibility may vary linearly along its length or by some other factor.

In the embodiments described above, the rings 12 of the articulation joint are cut into blank tubular stock made out of metal, such as stainless steel, with a laser or by some other technique such as electro-discharge machining. In some embodiments, it may be desirable to insert the springs in an uncut tube and to cut out the rings and bond the springs with the same device. In that case, it may be necessary to use two lasers, one of which is focused to cut the rings from the tube and the other of which is focused to bond the springs to the rings.

Figure 7A:
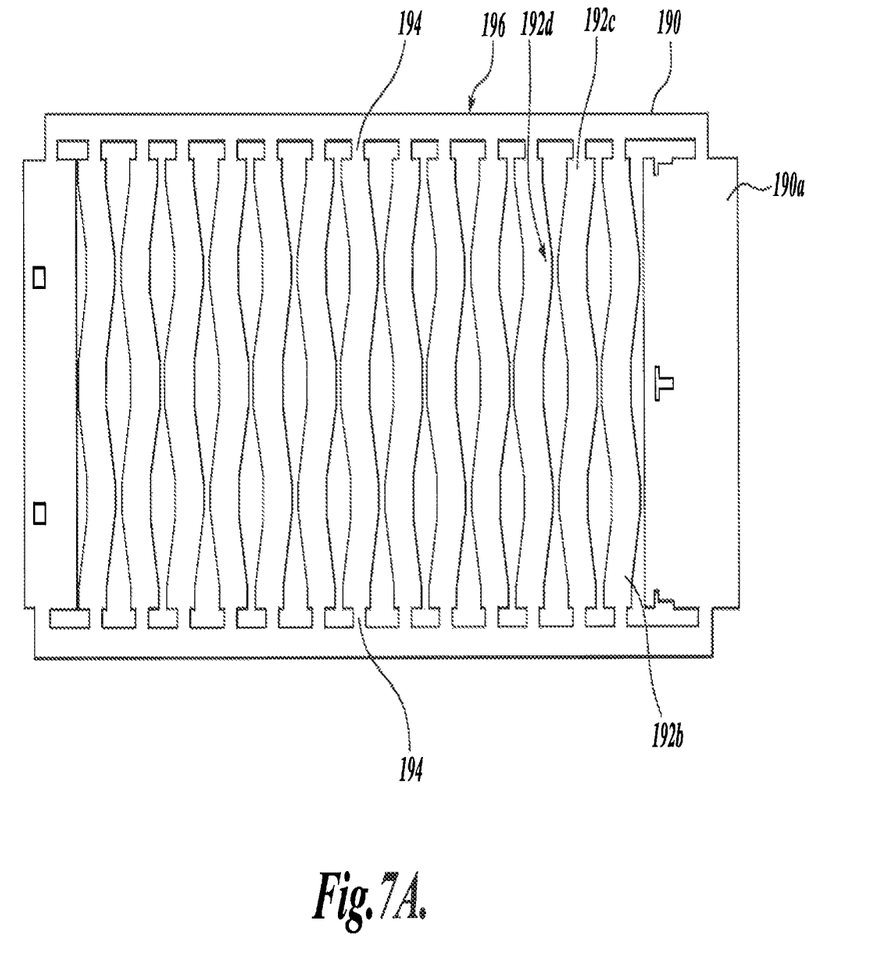
FIGS. 7A and 7B illustrate flat, metal sheets that are patterned to produce an articulation joint in accordance with an embodiment of the present invention.
Figure 7B:
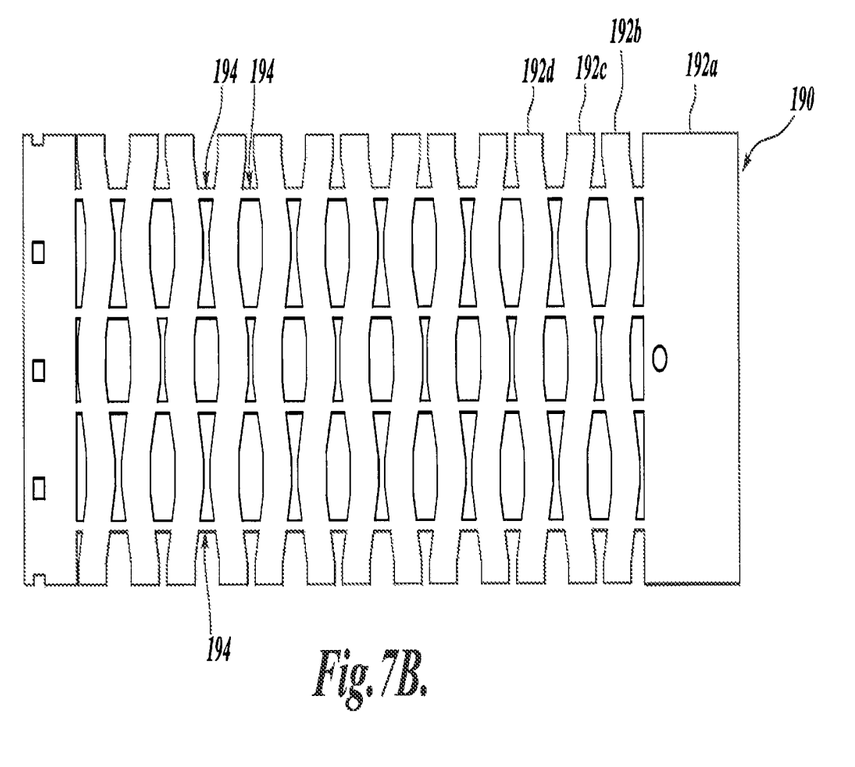

FIGS. 7A and 7B illustrate other techniques for manufacturing an articulation joint, such as articulation joint 10, in accordance with the present invention. Instead of cutting the pattern of rings from blank tubular stock, it is possible to form the pattern of rings from a blank sheet of stock material. In the example shown in FIG. 7A, a sheet 190 of stock material, such as a sheet stainless steel, has a pattern of ring segments 192*a*, 192*b*, 192*c*, etc., that are molded, cut (e.g., laser, waterjet, etc.), punched, stamped or otherwise formed into the sheet 190. In one embodiment, stamping the pattern into the sheet may allow the sheets to be easily manufactured with a high degree of uniformity. Additionally, for high volume manufacturing, a progressive stamping die could be used that is several feet in length and could stamp many articulation joints at once on a continuous process.

Each ring segment 192 of the articulation joint is held within the sheet by a tab 194 at either end of the ring segment, as shown in FIG. 7A. As long as at least one of the tabs 194 is intact, the individual ring segments in the sheet remain intact. Alternatively, the tabs 194 may be provided between adjacent ring segments to hold one ring to another, as shown in FIG. 7B. In these embodiments, it should be appreciated that the ring segments can have various different rim angles as described above.

Figure 8:
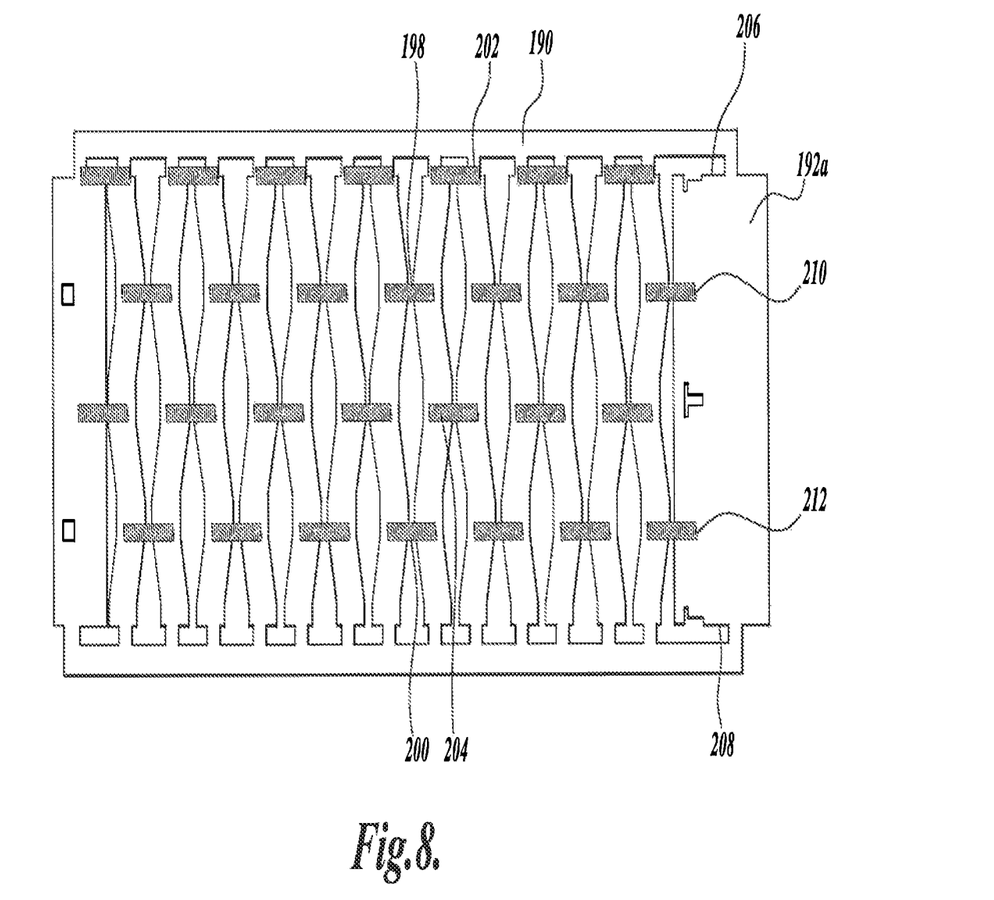
FIG. 8 illustrates a number of springs positioned on the patterned sheet shown in FIG. 7A for forming an articulation joint.

Once the ring segments are formed, the springs are arranged on the sheet in a desired pattern such as that shown in FIG. 8 and bonded thereto. In the embodiment shown, each pair of adjacent ring segments is joined with a pair of springs 198, 200, that are positioned so that they align 180 degrees apart in the final articulation joint assembly. The springs 204, 206 joining adjacent pairs of rings are alternately oriented at 90 degrees with respect to each other as described above. Again, the springs may comprise individual spring segments that are placed on the flat sheet 190 prior to bonding. Alternatively, the springs may be continuous lengths of springs that are welded or otherwise bonded at the appropriate places on the rings. The remainder or undesired portion of the springs may be removed with a laser or other means. Using individual spring segments allows the bending characteristics of the articulation joint to be tailored along its length or in any other desired direction.

Once the springs are bonded to the ring segments, the sheet 190 shown in FIG. 8 is appropriately worked into a tubular structure via any technique known in the metal forming arts (e.g., bending the sheet around a mandrel (not shown)) such that the ends of each ring segment, such as end 206 and end 208 of the distal ring 192*a*, either abut or overlap. The abutting or overlapping ends of the ring segments are then joined by welding, adhesive, bending, crimping, or the like to form the articulation joint. Once the ends are joined, the tabs 194 and/or other metal scrap material may then he removed via one of the numerous techniques described above.

Figure 9:
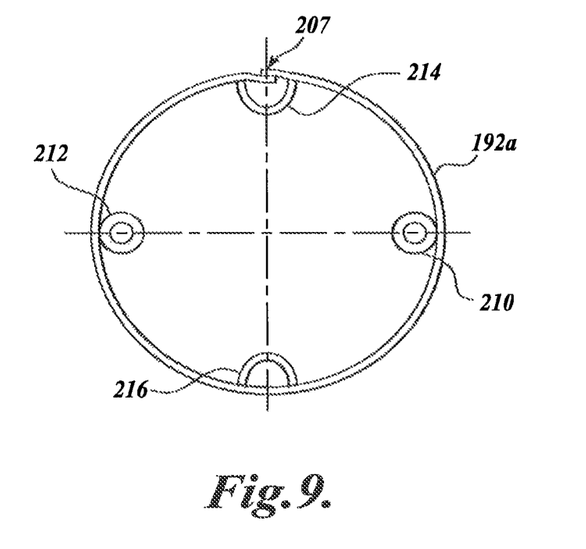
FIG. 9 is an end view of a ring of one embodiment of an articulation joint with a pair of springs bonded therein.

FIG. 9 shows an end view of the distal ring 192*a* of an articulation joint made in accordance with one embodiment of the present invention. As best shown in FIG. 9, the ends of the distal ring segment are overlapped at a point 207 and are welded or otherwise bonded together. The example shown in FIGS. 8 and 9 has the weld line on one of the axes of the joint. However, the weld line could be positioned anywhere around the circumference of the joint and does not need to he located on one of the axes. In this embodiment, the distal ring segment is formed into the distal ring such that the springs are disposed on the inside of the distal ring. The springs 210, 212 are oriented at 180 degrees apart to permit flexing of the articulation joint at an angle transverse to the axis of the aligned springs. As indicated above, the distal ring 192*a* may include one or more inwardly extending lances 214, 216 that form loops against which a ferrule of a control wire can engage. Because the control wires are routed through the holes in the springs and the springs are bonded to the rings, the springs 210, 212 in the distal ring can also serve as anchor points for control wires. While it has been described in these embodiments that the springs are bonded to the ring segments prior to metal working the sheet into a tubular structure, it will be appreciated that the springs may be bonded subsequent to the sheet being metal worked into a tubular structure to form the articulation joint. In this embodiment, the springs may be placed into the appropriate position by either fixture 100 or 150 described above. Once the springs are bonded to the rings, the tabs may then he removed.

Figure 10:
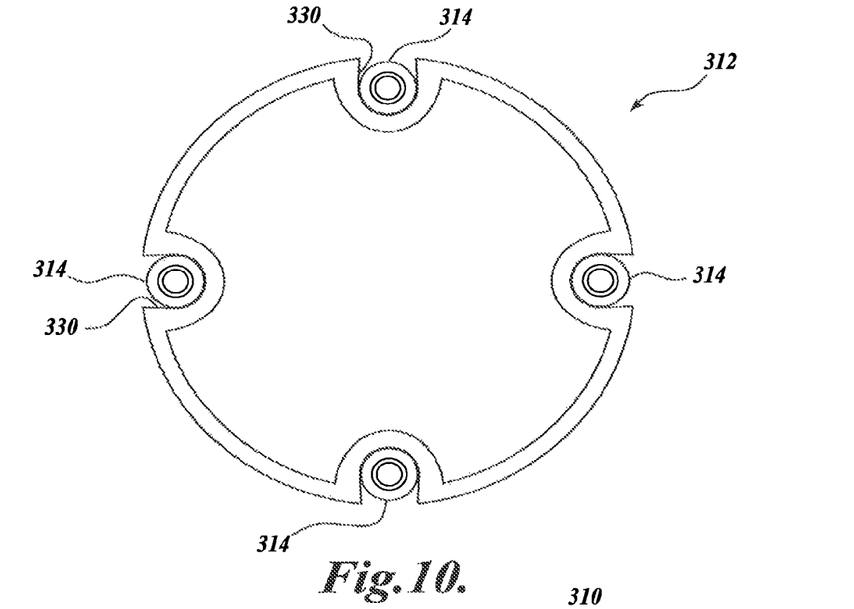
FIGS. 10 and 11 illustrate another embodiment of an articulation joint that can be manufactured in accordance with aspects of the present invention.
Figure 11:
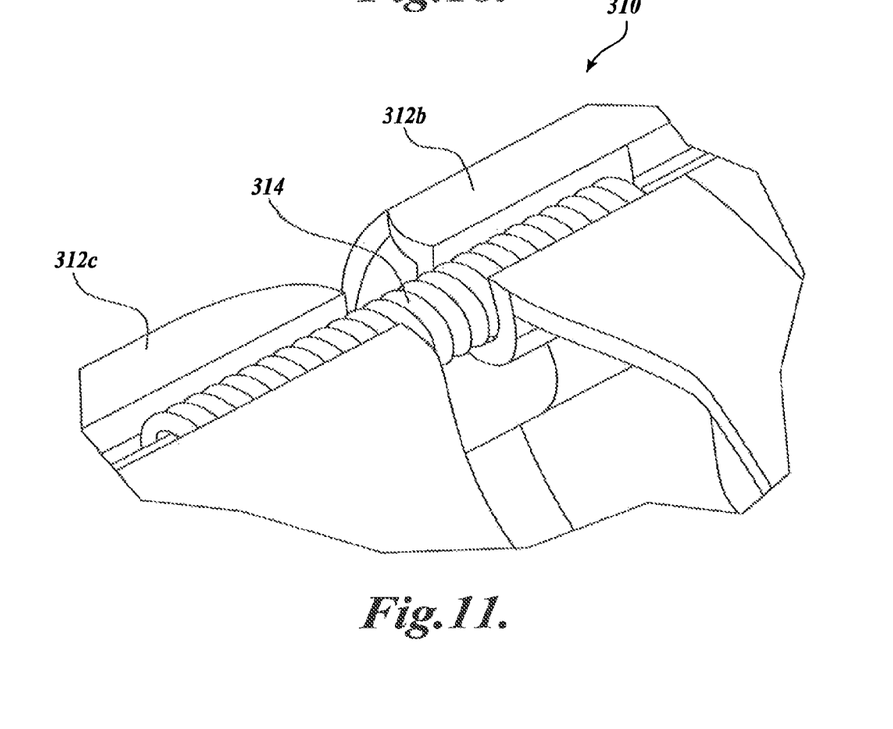

FIGS. 10 and 11 illustrates another technique for manufacturing an articulation joint in accordance with the present invention. In this embodiment, the rings 312*a*, 312*b*, etc., of the articulation joint 310 are formed with slots or channels 330 spaced 90 degrees apart around the circumference of the rings. The slots or channels 330 are formed so as to open outwardly from the rings, as best shown in FIG. 10.

The rings may either be formed from blank tubular stock, such as a stainless steel tube, or a sheet of flat stock, such as a sheet of stainless steel. In either case, the stock is appropriately metal formed by any technique known in the art so that the slots or channels are disposed 90 degrees from one another and open outwardly, as described above. When starting with a sheet of flat stock, the sheet may be metal formed into a tubular structure prior to or after the slots are formed. Additional processes for forming the rings/ring segments may be performed prior to or after slot formation via any one of the techniques described above, e.g., laser cutting, stamping, punching, etc, In these embodiments, it should be appreciated that the rings can have various different rim angles as described above.

The slots or channels 330 are preferably formed as being slightly oversized with respect to the diameter of the springs to be used. The springs 314 are then laid into position for adjacent rings, as best shown in FIG. 11, and secured into place via appropriate techniques, such as crimping, swaging, heat bonding, welding, adhesive gluing, just to name a few. This step is repeated until the articulation joint is complete.

Once the springs 314 are received in and bonded to the rings 312, additional steps may be performed such as flaring one or more of the rings. In the example shown in FIG. 1A, the distal ring is flared slightly to engage other components of the medical device. In addition, any burrs of the joint may be removed.

This embodiment gives improved articulation performance because it requires less torque to articulate the tip since the steering cables are disposed on the outside of the ring and therefore are further from the pivot points. This provides a greater mechanical advantage to articulate the distal end of the medical device about the articulation joint.

In order to further improve the torque transfer characteristics of an articulation joint and to have a smoother outer surface of the joint for passing through body cavities and to ensure the plastic cover of the bending section does not get pinched between the rings during bending, the joint may include a braided sheath (not shown) that is bonded to the proximal and distal rings with an adhesive or the like. In one embodiment, the sheath is formed of a wire braid of 48 carriers, 8 wires per carrier, of 42 gauge wire. The wires are wound at 32.4 pie/inch on a 0.500 inch core. A thermally activated adhesive or a UV curable adhesive may be used. Any additional loose strands of the braid are then held in place by applying a thin layer of tape over the braid ends. Teflon or Kapton tape may be used. Alternatively, the ends of the braid may be brazed, welded or soldered to the links of the articulation joint. Other methods, suitable for low cost high volume, of attaching the braid ends include swaging or crimping a metal ring over the top of the braid ends or wrapping the ends of the braid with a tightly wound wire.

Alternative sheaths can be made of nylon or polyester. These sheaths can be braided on a core as described above and then cut into sections and bonded to the articulation joints. Alternatively, the finished articulation joints can be stacked on a mandrel to form a continuous feed of articulation joints which are then fed through a braiding machine. In this embodiment, the articulation joints serve as a flexible core to wind the braid on.

Figures 12A, 12B:
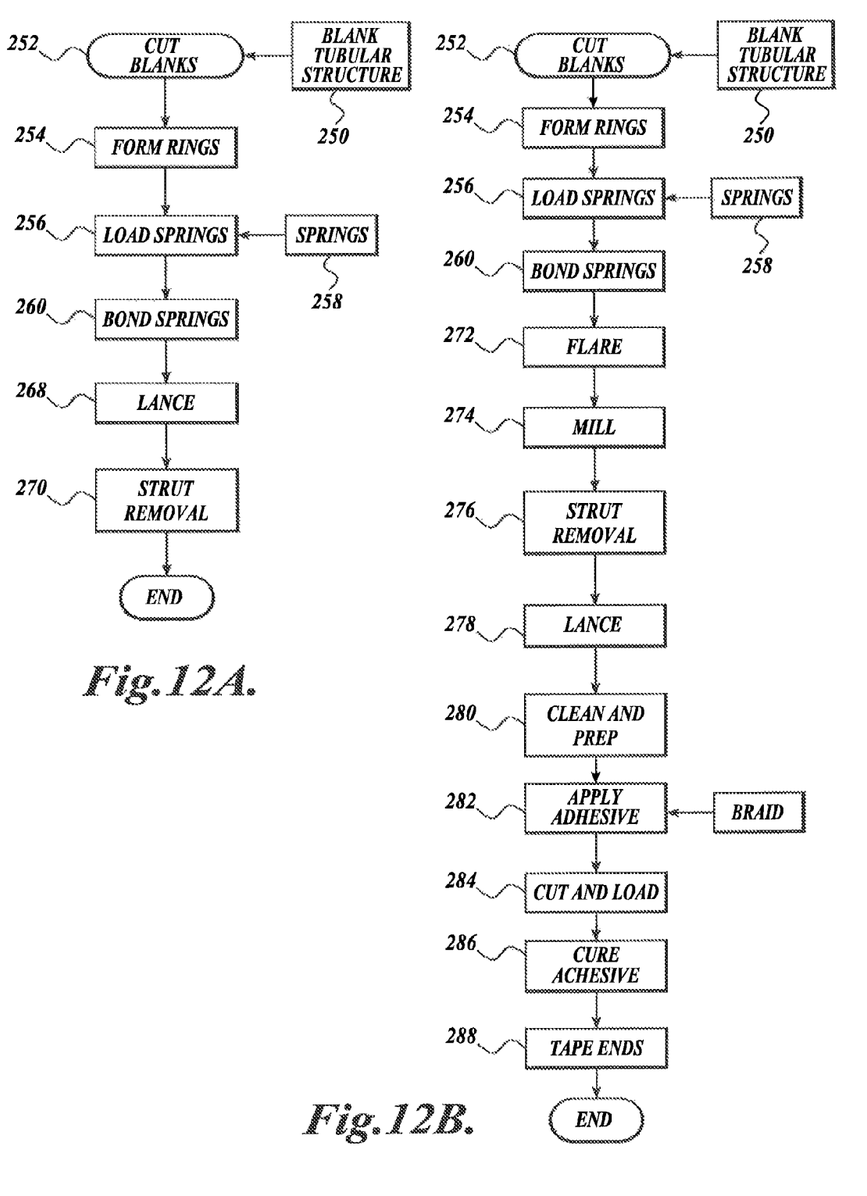
FIGS. 12A and 12B are flow charts of methods of forming an articulation joint in accordance with embodiments of the present invention.

FIGS. 12A and 12B are flow charts showing a number of steps performed when creating articulation joints in accordance with embodiments of the present invention. In one embodiment shown in FIG. 12A, a blank tubular structure is obtained at step 250 and the rings of the joint are formed into the tubular structure at steps 252 and 254. The blank tubular structure may be obtained from blank tubular stock or from a blank sheet of metal stock processed in an appropriate manner. At step 256, the springs are loaded into the tubular structure with a fixture, such as fixture 100 or 150.

The springs are then bonded, for example, laser welded, to the rings at step 260. As indicated above, in one embodiment, the rings are compressed onto the springs prior to bonding to ensure a good bond. At 268, lances may be optionally added and the struts or tabs that join adjacent rings may be removed at 270.

FIG. 12B shows some additional processing steps that may be performed. Again, a blank tubular structure is obtained and rings are formed therein at steps 250-254. Alternatively, the rings may be preformed in the tube as described above. At step 256-260, the springs are bonded to the inner surface of the rings. At 272, any rings are flared if desired and the articulation joint is milled to add any required features at 274. Struts or tabs between the rings of the joint, if present, may be removed at step 276. At 278, any optional lances may be added to the distal ring to provide an anchor point for one or more of the control wires that bend the articulation joint.

The articulation joint is cleaned and prepped at step 280 to remove any burrs and manufacturing oils so that an optional braid can be secured to the joint. At step 282, adhesive is applied to the proximal and distal ring. A suitable length of braid is cut and placed over the joint at step 284. The adhesive is cured by the application of heat, UV, or other adhesive curing energy at step 286. Finally, the ends of the braid are taped at step 288 to help prevent fraying.

Figure 13A:
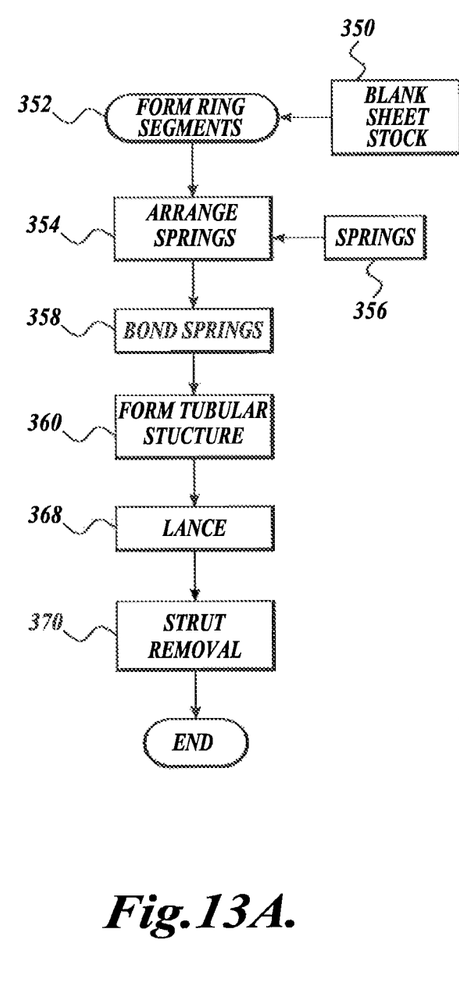
FIGS. 13A and 13B are flow charts of methods of forming an articulation joint in accordance with other embodiments of the present invention.
Figure 13B:
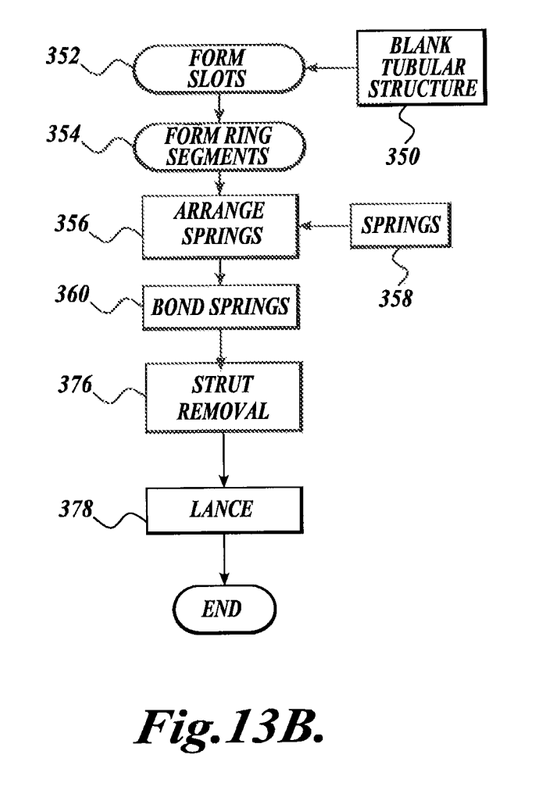

FIGS. 13A and 13B are flow charts showing a number of steps performed when creating articulation joints in accordance with additional embodiments of the present invention, In one embodiment shown in FIG. 13A, a sheet of stock material, such as a sheet of stainless steel, is obtained at step 350 and ring segments are formed therein via cutting, stamping, punching, etc., at steps 352. At steps 354 and 358, the springs are arranged on the sheet and bonded to adjacent ring segments, as shown, for example, in FIG. 7A or 7B. The sheet of ring segments and springs is then formed into a tubular structure at step 360. At 368, lances may be optionally added and the struts or tabs that join adjacent rings may he removed at 370, Additional steps may be performed, such as those described as steps 272-288 in FIG. 12B.

In an alternative method of manufacturing the articulation joint, the sheet of stock material may be formed as a tubular structure prior to bonding the springs to the ring segments. In this embodiment, the springs may be held in place by one of the fixtures 100 or 150 and bonded to the rings as described above.

In the embodiment shown in FIG. 13B, a blank tubular structure is obtained at step 350. The blank tubular structure may be obtained from blank tubular stock or from a blank sheet of metal stock processed in an appropriate manner. At step 352, slots are formed as shown in FIG. 10 and the ring segments are formed via laser cutting, stamping, punching, etc., at steps 354. At 356, the springs are placed in the slots of adjacent rings and secured to the rings via crimping, swaging, etc., at step 360. At 376, the struts or tabs that join adjacent rings may be removed and the lances in the joint may be optionally added at 378. Additional steps may be performed, such as those described as steps 272-288 in FIG. 12B.

While illustrative embodiments have been illustrated and described, it will be appreciated that various changes can be made therein without departing from the spirit of the invention. For example, the ends of the braid may be fused together with paint or adhesive before the braid is cut. The braid is then cut through the center of these painted areas ensuring that both ends of the braid are fused and have no exposed wires. If a metal braid is used, the braid can be welded, soldered or braised to the end link of the articulation joint.

It is therefore intended that the scope of the invention be determined from the following claims and equivalents thereof.

The embodiments of the invention in which an exclusive property or privilege is claimed are defined as follows:

1. A method of constructing an articulation joint, the articulation joint including a elongate tube having a plurality of articulation segments connected to one another by at least one spring, the method comprising the steps of:
   forming a pattern of the plurality of articulation segments in a sheet of metal;
   forming the plurality of articulation segments into at least a partial tubular structure; and
   coupling at least one spring to the plurality of articulation segments, wherein the at least one spring has a length extending substantially parallel to a longitudinal axis of the articulation joint.

2. The method of claim 1, wherein forming at least part of the pattern includes at least one of laser cutting, water jet cutting, and electro-discharge machining.

3. The method of claim 1, further including cutting the at least one spring.

4. The method of claim 3, wherein cutting the at least one spring includes at least one of laser cutting and electro-discharge machining.

5. The method of claim 1, wherein the at least one spring is coupled to the plurality of articulation segments using at least one of welding, adhesive gluing, bending, crimping, swaging, and heat bonding.

6. The method of claim 1, wherein the articulation segments include at least one of a curved surface and a flat surface.

7. The method of claim 1, wherein forming the at least partially tubular structure includes folding the sheet of tubular metal about a fixture configured to receive the at least one spring.

8. The method of claim 1, wherein the at least one spring includes a plurality of springs.

9. The method of claim 1, wherein, in a final construction, each articulation segment of the plurality of articulation segments includes a top rim and a bottom rim that is not planar with a longitudinal axis of the articulation segment.

10. The method of claim 1, wherein at least one spring extends through at least one articulation segment.

11. The method of claim 1, wherein at least one spring extends through adjacent articulation segments.

12. The method of claim 1, wherein:
   at least one spring includes a plurality of springs; and
   radially adjacent springs are longitudinally staggered.

13. The method of claim 1, wherein adjacent articulation segments are joined by a plurality of springs.

14. A method of constructing an articulation joint, the articulation joint including a elongate tube having a plurality of articulation segments connected to one another by a plurality of springs, the method comprising the steps of:
   forming a pattern of the plurality of articulation segments in a sheet of metal;
   forming the plurality of articulation segments into at least a partial tubular structure; and
   coupling the plurality of springs to the plurality of articulation segments, wherein at least one of the plurality of springs extends through at least one articulation segment.

15. The method of claim 14, wherein at least one of the plurality of springs extends through adjacent articulation segments.

16. The method of claim 14, wherein radially adjacent springs are longitudinally staggered.

17. The method of claim 14, wherein adjacent articulation segments are joined by a plurality of springs.

* * * * *

UNITED STATES PATENT AND TRADEMARK OFFICE
CERTIFICATE OF CORRECTION

PATENT NO. : 8,567,033 B2  Page 1 of 1
APPLICATION NO. : 13/227878
DATED : October 29, 2013
INVENTOR(S) : Macnamara It is certified that error appears in the above-identified patent and that said Letters Patent is hereby corrected as shown below:

On the title page, under Item [60] titled RELATED U.S. APPLICATION DATA, "Provisional application No. 60/795,119," should read --Provisional application No. 60/792,119--.

Signed and Sealed this
Twenty-fourth Day of December, 2013

Margaret A. Focarino
*Commissioner for Patents of the United States Patent and Trademark Office*